United States Patent [19]
Irie et al.

[11] Patent Number: 5,646,154
[45] Date of Patent: Jul. 8, 1997

[54] PHARMACEUTICAL COMPOSITIONS FOR INHIBITING THE FORMATION OF TUMOR NECROSIS FACTOR

[75] Inventors: Kenji Irie, Nishinomiya; Yutaka Ueda; Norio Fujiwara, both of Toyonaka, all of Japan

[73] Assignee: Sumitomo Pharmaceuticals Co., Ltd., Osaka, Japan

[21] Appl. No.: 411,595

[22] PCT Filed: Oct. 7, 1993

[86] PCT No.: PCT/JP93/01443

§ 371 Date: May 12, 1995

§ 102(e) Date: May 12, 1995

[87] PCT Pub. No.: WO94/07498

PCT Pub. Date: Apr. 14, 1994

[30] Foreign Application Priority Data

Oct. 7, 1992 [JP] Japan .................. 4-296457

[51] Int. Cl.$^6$ .................................. A01N 43/54
[52] U.S. Cl. .............. 514/260; 435/69.5; 435/252.33; 435/254.11; 514/247; 514/257; 514/259; 540/582; 540/600; 544/292
[58] Field of Search ................... 514/247, 257, 514/259, 260; 540/582, 600; 544/292; 435/69.5, 252.33, 254.11

[56] References Cited

U.S. PATENT DOCUMENTS 3,305,553  2/1967  Hoefle et al. .............. 540/600

FOREIGN PATENT DOCUMENTS 5888369  5/1983  Japan .

*Primary Examiner*—Terressa Mosley
*Attorney, Agent, or Firm*—Sughrue, Mion, Zinn, Macpeak & Seas

[57] ABSTRACT

Quinazoline compounds represented by general formula (1) or (2) possess an activity of significantly inhibiting the production or secretion of a tumor necrosis factor and are useful as drugs for the treatment of diseases wherein a tumor necrosis factor is considered to be involved in causing those diseases:

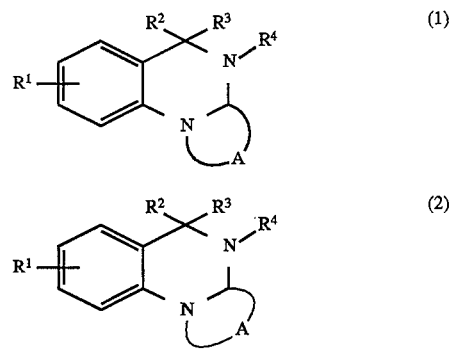

wherein $R^1$ through $R^7$ and A represent specific functional groups

4 Claims, 2 Drawing Sheets

PROTECTIVE EFFECT ON ENDOTOXIN—INDUCED DEATH IN GALACTOSAMINE—TREATED MICE $*: p<0.05,  **: p<0.01$

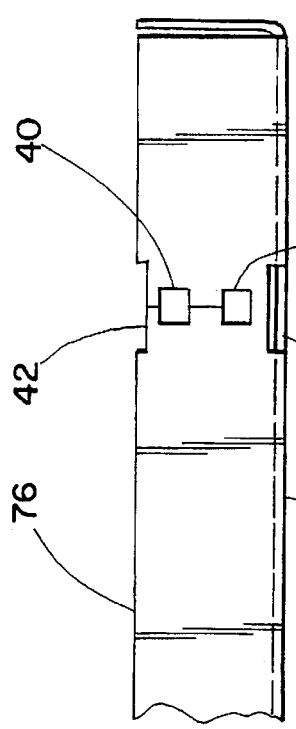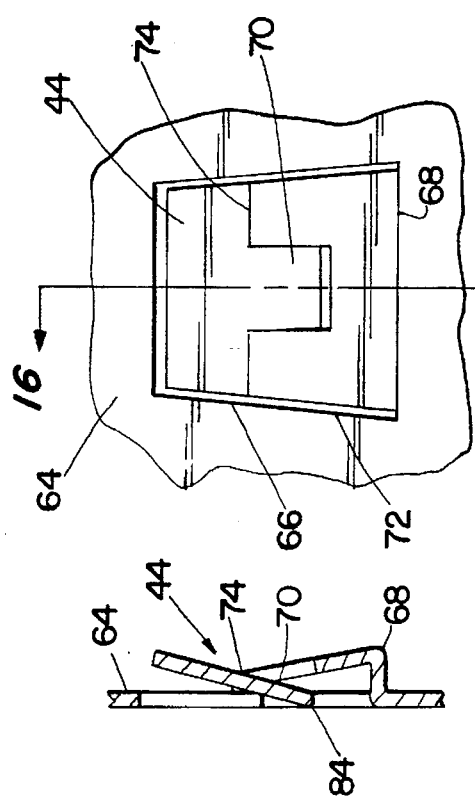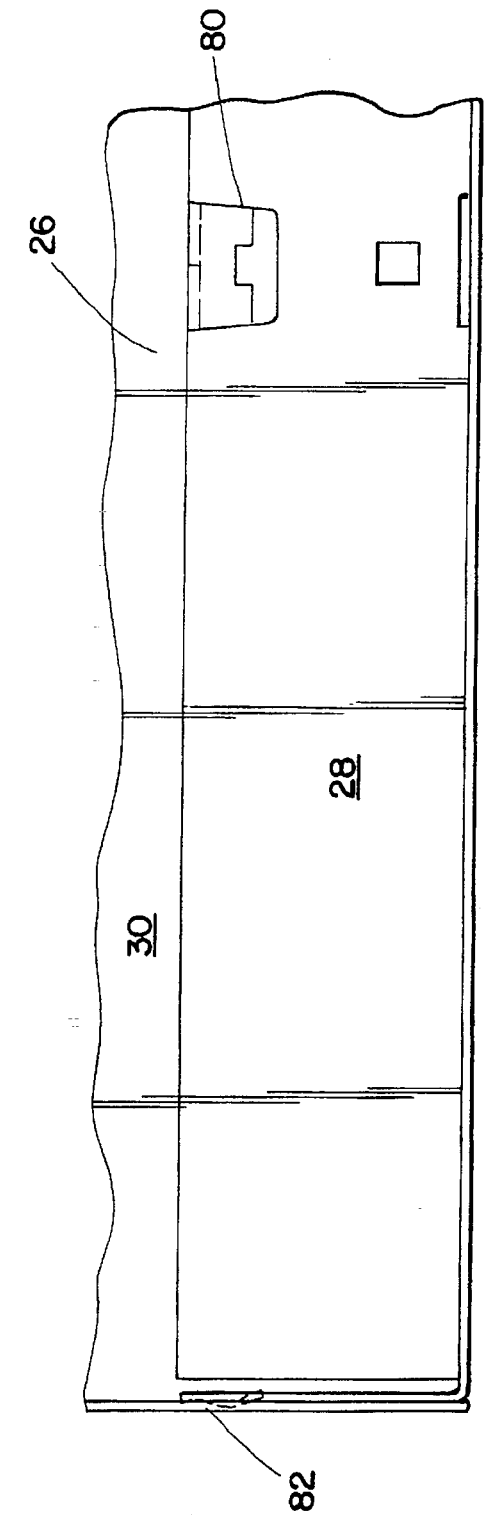

INHIBITION OF TNF FORMATION IN ENDOTOXIN SHOCK IN GALACTOSAMINE-TREATED MICE $*: p<0.05, **: p<0.01$

PHARMACEUTICAL COMPOSITIONS FOR INHIBITING THE FORMATION OF TUMOR NECROSIS FACTOR

TECHNICAL FIELD

The present invention relates to a pharmaceutical composition for inhibiting the formation or secretion of a tumor necrosis factor. More particularly, the present invention relates to a pharmaceutical composition inhibiting the formation or secretion of a tumor necrosis factor, which comprises a quinazoline compound or salts thereof as an effective ingredient and which is effective for the treatment of diseases including cachexia, sepsis and multiple organ failure wherein a tumor necrosis factor is considered to be involved in causing those diseases.

BACKGROUND ART

A tumor necrosis factor (hereinafter abbreviated as TNF) is a peptide of 157 amino acids, having a molecular weight of about 17,000. TNF is one of cytokines produced by various cells including macrophages.

Although TNF had been at first found as a cytokine showing a cytotoxic effect on tumor, subsequent studies have revealed that the activities of TNF are various, and not only limited to tumor cells but also extended to many other normal cells. Examples of such TNF activities include suppression of the lipoprotein lipase activity in adipocytes, expression of HLA antigen on blood endothelial cells and fibroblasts, interleukin-1 formation by fibroblasts or macrophages, activation of cytotoxic macrophages, suppression of CFU, formation of colony stimulating factor by fibroblasts, endothelial cells or some tumor cells, inhibition of the synthesis of proteoglycans and stimulation of their resorption in cartilage, activation of neutrophils and generation of superoxide, formation of procoagulant factor by blood endothelial cells, proliferation of fibroblasts, change in membrane potential of skeletal muscle, interferon $\beta_2$ production by fibroblasts, and injury of blood endothelial cells. In these days, TNF has thus been recognized to be a cytokine which are involved broadly in vital protection through inflammation and immune response (Ann. Rev. Immunol., 10, 411 (1992)).

On the other hand, it has been found that continuous or excessive formation of TNF rather results in vigorous actions on normal cells to cause various diseases. It is also reported that TNF is known as cachectin which induces cachexia in cancer or infectious diseases which causes catabolic acceleration of total metabolism to lead to extreme wasting (B. Beutler, D. Greenwald, J. D. Hulmes et al., Nature, 316, 552–554 (1985), Kawakami, M., SEIKA-GAKU (Biochemistry), 59, 1244–1247 (1987)).

An anti-TNF antibody is considered to be effective also for a septic shock (Starnes, H. F. Jr., Pearce, M. K., Tewari, A., Yim, J. H., Zou, J-C., Abrams, J. S., J. Immunol., 145, 4185–4191 (1990), Beutler, B., Milsark, I. W., Cerami, A. C., Science, 229, 869–871 (1985), Hinshaw, L. B., Tekamp-Olson, P., Chang, A. C. K. et al., Circ. Shock, 30, 279–292 (1990)).

An increased level of TNF is also observed in the synovial fluid or blood from patients with rheumatoid arthritis (Tetta, C., Camussi, G., Modena, V., Vittorio, C. D., Baglioni, C., Ann. Rheum. Dis., 49, 665–667 (1990)).

In addition, it is reported that there are many other diseases wherein a TNF level increase in blood, e.g., Kawasaki disease (Matsubara, T., Furukawa, S., Yabuta, K., Clin. Immunol. Immunopathol., 56, 29–36 (1990)); ulcerative colitis (Murch, S., Walker-Smith, J. A., Arch. Dis. Child, 66, 561 (1991)); Behçet disease (Akoglu, T., Direskeneli, H., Yazici, H., Lawrence, R., J. Rheumatol., 17, 1107–1108 (1990)); systemic lupus erythematosus (SLE) (Maury, C. P. J., Teppo, A-M., Arthritis Rheum., 32, 146–150 (1989)); graft versus host disease (GvHD) (J. Exp. Med., 175, 405–413 (1992)); multiple organ failure (Kawakami, M., Hayata, K., Medical Immunology, 20, 615–620 (1990)); malaria (Grau, G. E., Fajardo, L. F., Piguet, P. F., et al., Science, 237, 1210–1212 (1987)); acquired immune deficiency syndrome (AIDS) (Kawakami, M., Hayata K., Medical Immunology, 20, 615–620 (1990)); meningitis (Waage, A., Halstensen, A., Espevik, T., Lancet, I, 355–357 (1987)); fulminant hepatitis (Sugano, K., KANZO (Liver), 33, 213–218 (1992)); and inflammatory Bowel disease (Maeda, M., SHOKAKI-TO- MEN-EKI (Digestive Organ and Immunity), 22, 111–114 (1989)).

From the above publications, it is understood that excessive formation of TNF sometimes adversely affect the living body. Therefore, further investigations are desired to develop TNF inhibitors available for the treatment of these diseases.

Pentoxifylline having a methylxanthine skeleton is known as a compound showing an activity of inhibiting TNF. It is reported that this compound possesses an activity of preventing death in endotoxin-shocked mice, an activity of improving the sense of well-being or preventing a weight loss in severe pulmonary tuberculosis patients or cancer patients (Zabel, P., Schade, F. U., Schlaak, M., Immunobiol., 187, 447–463 (1993), Dezube, B. J., Pardee, A. B., et al., Cancer Immuno. Immunother., 36, 57–60 (1993)).

In addition, glucocorticoid, protease inhibitors, phospholipase $A_2$ inhibitors, lipoxygenase inhibitors, PAF (platelet aggregating factor) antagonists, radical scavengers, prostaglandin $F_2$ or $I_2$ and anti-TNF antibody are heretofore known as compounds or factors for showing a TNF inhibitory activity.

In the future, the function of TNF in association with diseases will be made clearer, using these low molecular compounds or antibodies. However, these compounds are accompanied by side effects due to a wide variety of the pharmacological activities. Therefore, it is desired to develop highly safe compounds based on a novel mechanism.

The present invention provides a therapeutic drug for diseases which TNF would cause, due to its inhibition against TNF formation or secretion. Such diseases include cachexia, sepsis, multiple organ failure, rheumatoid arthritis, ulcerative colitis, Behçet disease, systenic lupus erythematosus (SLE), graft versus host disease (GvHD), malaria, acquired immune deficiency syndrome (AIDS), meningitis, fuluminant hepatitis, and inflammatory Bowel disease.

The compounds which are used as the active ingredient in the present invention are known and disclosed, with their syntheses or anti-inflammatory or analgesic use, in, e.g., Chem. Pharm. Bull., 29 (8), 2135–2156 (1981), Synthetic Communications, 10 (11), 805–811 (1980), Chem. Pharm. Bull., 26 (6), 1633–1651 (1978), Japanese Patent Application KOKAI Nos. 53-23997, 53-12893, 52-71483, 52-51379, 51-8287, 51-100098 and 47-14183, Arzneim-Forsch., 22 (11), 1958–1962 (1972), U.S. Pat. No. 3,305, 553, etc. However, these publications are totally silent on the activity of inhibiting the formation or secretion of TNF in accordance with the present invention.

DISCLOSURE OF THE INVENTION

The present inventors have discovered that quinazoline compounds exert on a potent activity of inhibiting the formation or secretion of TNF and have come to accomplish the present invention.

That is, an object of the present invention is to provide a pharmaceutical composition for inhibiting the formation or secretion of TNF, and comprising as an active ingredient a compound represented by general formula (1) below:

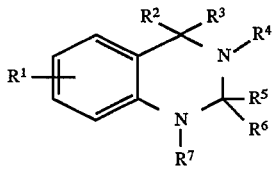

(1)

wherein $R^1$ represents a hydrogen atom, a halogen atom, a hydroxy group, an amino group, a substituted amino group, a nitro group, a cyano group, an alkyl group, an alkoxy group, an alkylthio group, an acyl group, a carboxyl group or an alkoxycarbonyl group; $R^2$ represents a phenyl group, a substituted phenyl group, a thienyl group, a furyl group, a cycloalkyl group, a cycloalkenyl group, an alkyl group, an amino group or a substituted amino group; $R^3$ represents a hydrogen atom and $R^4$ represents a hydrogen atom or an alkyl group, or $R^3$ and $R^4$ are combined together to form a bond; in $R^5$, $R^6$ and $R^7$, $R^5$ and $R^6$ are combined together to form an oxo group or a thioxo group and $R^7$ represents a hydrogen atom, an alkyl group, a haloalkyl group, a phenyl group, a substituted phenyl group or a group shown by formula: —X—Y (wherein X represents an alkylene group and Y represents a cycloalkyl group, a phenyl group, a substituted phenyl group, a carboxyl group, a hydroxy group, an alkoxy group, an aminocarbonyl group, a substituted aminocarbonyl group, an alkoxycarbonyl group, an amino group or a substituted amino group), or, $R^6$ and $R^7$ are combined together to form a bond and $R^5$ represents a hydrogen atom, an alkyl group, an amino group, a halogen atom, a haloalkyl group, a hydroxyamino group, a hydrazino group, an alkylhydrazino group, an acylhydrazino group or an acylamino group; or a compound represented by general formula (2) below:

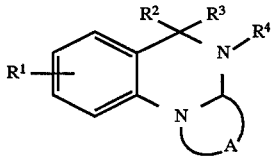

(2)

wherein $R^1$, $R^2$, $R^3$ and $R^4$ represent the same significance as described above and the formula therein:

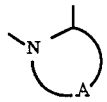

represents a heterocyclic group containing 2 to 4 nitrogen atoms; or a salt thereof.

Another object of the present invention is to provide a method for inhibiting the formation or secretion of TNF which comprises administering to human an effective dose of the compound represented by general formula (1) or (2) described above, or a salt thereof.

A further object of the present invention is to provide use of these compounds or salts thereof for preparing the pharmaceutical composition for the formation or secretion of TNF comprising the compound represented by general formula (1) or (2) described above, or a salt thereof.

Figure 2:
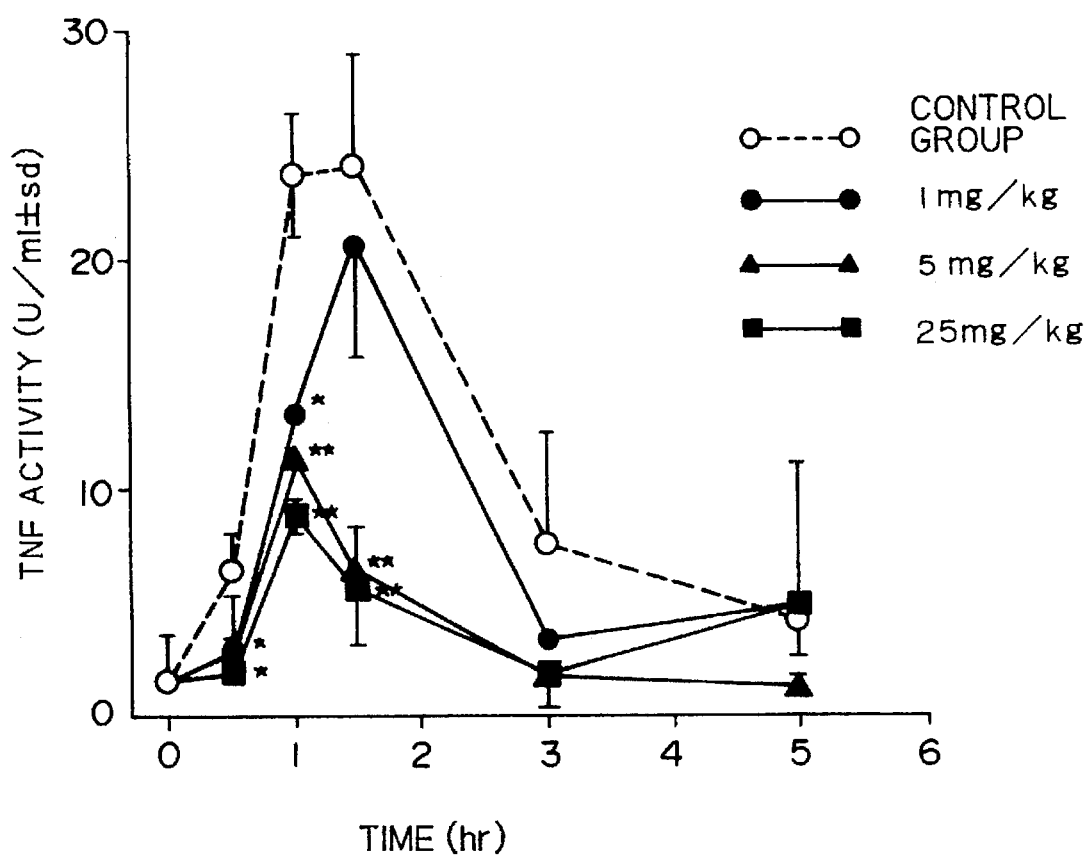
FIG. 2 is a graph showing the results of a test performed in Test Example 3 herein, in which an effect of inhibiting the formation or secretion of TNF was examined in mice with galactosamine-treated endotoxin shock.

In the graphs, the abscissa designates a time period passed after administration of LPS, D-galN and 5% dimethylsulfoxide-10% Nikkol solution (control group) or administration of LPS, D-galN and Compound No. 33 in Example 1 in 3 concentrations; the ordinate designates a TNF activity in serum collected from mice (3 in each group) at each passage time. The TNF activity (U/ml) is expressed by a mean value of the data measured with serum from 3 mice and standard deviation (s.d.).

BEST MODE FOR CARRYING OUT THE INVENTION

The functional groups in the compounds of the present invention represented by general formula (1) or general formula (2) are described below.

As the alkyl group, the alkoxy group and the alkylthio group, a lower alkyl group, a lower alkoxy group and a lower alkylthio group are preferred, respectively. As the acyl group, preferred are a lower alkanoyl group and an aroyl group. As the alkoxycarbonyl group, the cycloalkyl group, the cycloalkenyl group, the haloalkyl group, the alkylene group, the alkylhydrazino group, the acylhydrazino group and the acylamino group, preferred are a lower alkoxycarbonyl group, a lower cycloalkyl group, a lower cycloalkenyl group, a halo-lower alkyl group, a lower alkylene group, a lower alkylhydrazino group, a lower alkanoylhydrazino group and a lower alkanoylamino group, respectively.

Examples of the halogen atom include fluorine, chlorine, bromine and iodine.

Specific examples of the lower alkyl group include an alkyl group having 1 to 6 carbon atoms, such as methyl, ethyl, propyl, butyl, pentyl, hexyl, 1-methylethyl, 1-methylpropyl, 2-methylpropyl, 1-ethylpropyl, 2-ethylpropyl, 1-methylbutyl, 2-methylbutyl, 3-methylbutyl, 1-ethylbutyl, 2-ethylbutyl, 3-ethylbutyl, 1-methylpentyl, 2-methylpentyl, 3-methylpentyl, and 4-methylpentyl.

As the lower alkoxy group, there are an alkoxy group having 1 to 6 carbon atoms, such as methoxy, ethoxy, propoxy and butoxy.

As the lower alkylthio group, there are alkylthio group having 1 to 6 carbon atoms, such as methylthio, ethylthio, propylthio and butylthio.

As the lower alkanoyl group, there are an alkanoyl group having 1 to 6 carbon atoms, such as formyl, acetyl, propanoyl and butanoyl.

The aroyl group is an aroyl group having up to 11 carbon atoms and specific examples include benzoyl, 1-naphthoyl and 2-naphthoyl.

The lower alkoxycarbonyl group includes an alkoxycarbonyl group having 1 to 6 carbon atoms and specific examples are methoxycarbonyl, ethoxycarbonyl, propoxycarbonyl, butoxycarbonyl, and the like.

The lower cycloalkyl group includes a cycloalkyl group having 3 to 6 carbon atoms and specific examples are cyclopropyl, cyclobutyl, cyclopentyl, cyclohexyl, and the like.

The lower cycloalkenyl group includes a cycloalkenyl group having 3 to 6 carbon atoms and specific examples are 1-cyclohexenyl, 2-cyclohexenyl, 3-cyclohexenyl, and the like.

The halo-lower alkyl group includes a haloalkyl group having 1 to 6 carbon atoms and substituted with the halogen atom described above; specific examples are trifluoromethyl, 1,1,1-trifluoroethyl, 1,1,1,2,2-pentafluoroethyl, and the like.

As the substituted phenyl group there are phenyl groups substituted with, e.g., an alkyl group, an alkoxy group, a halogen atom, an alkylthio group or an acyl group. Specific examples include 4-chlorophenyl, 3-chlorophenyl, 2-chlorophenyl, 4-methoxyphenyl and 2-fluorophenyl.

As the thienyl group, there are, for example, 2-thienyl and 3-thienyl.

As the furyl group, there are, for example, 2-furyl and 3-furyl.

The lower alkylene group includes an alkylene group having 1 to 4 carbon atoms, such as methylene, ethylene, trimethylene, tetramethylene, 1-methylethylene, 2-methylethylene, 1,2-dimethylethylene, 1-ethylethylene, 2-ethylethylene, 1-methyltrimethylene, 2-methyltrimethylene and 3-methyltrimethylene.

The lower alkylhydrazino group includes an alkylhydrazino group having 1 to 6 carbon atoms and specific examples are N-methylhydrazino, N-ethylhydrazino, N-propylhydrazino, N-butylhydrazino, N-pentylhydrazino, N-hexylhydrazino, N'-methylhydrazino, N'-ethylhydrazino, N'-propylhydrazino, N'-butylhydrazino, N'-pentylhydrazino, N'-hexylhydrazino, and the like.

The lower alkanoylhydrazino group includes an alkanoylhydrazino group containing a lower alkanoyl group having 1 to 6 carbon atoms and specific examples are N-formylhydrazino, N-acetylhydrazino, N-propanoylhydrazino, N-butanoylhydrazino, N'-formylhydrazino, N'-acetylhydrazino, N'-propanoylhydrazino, N'-butanoylhydrazino, and the like.

As the substituted aminocarbonyl group, mention may be made of an aminocarbonyl group in which one or two alkyl groups are substituted and examples of the alkyl substituent include a lower alkyl group. More specific examples include an alkylaminocarbonyl group containing an alkyl group having 1 to 6 carbon atoms such as methylaminocarbonyl or ethylaminocarbonyl; and a dialkylaminocarbonyl group containing two alkyl groups which may be the same or different and have 1 to 6 carbon atoms, such as dimethylaminocarbonyl, diethylaminocarbonyl and ethylmethylaminocarbonyl. A further example of the substituted aminocarbonyl group includes a cyclic aminocarbonyl group. More specifically, the cyclic aminocarbonyl group includes a cyclic aminocarbonyl group having 5 to 6 carbon atoms in which the ring containing the nitrogen atom is 5 or 6 members. Specific examples of such cyclic aminocarbonyl group include 1-pyrrolidinocarbonyl and 1-piperidinocarbonyl.

The substituted amino group includes an amino group in which, e.g., one or two alkyl groups are substituted and an example of the alkyl substituent is a lower alkyl group. More specific examples include an alkylamino group containing an alkyl group having 1 to 6 carbon atoms such as methylamino, ethylamino, etc.; and a dialkylamino group containing two alkyl groups which may be the same or different and have 1 to 6 carbon atoms, such as dimethylamino, diethylamino and ethylmethylamino. A further example of the substituted amino group includes a cyclic amino group. As the cyclic amino group, mention may be made of a cyclic amino group having 4 to 5 carbon atoms, in which the ring containing the nitrogen atom is 5- or 6-members. Specific examples are 1-pyrrolidino and 1-piperidino.

As the heterocyclic structure containing 2 to 4 nitrogen atoms, there are 5-membered heterocyclic rings containing an oxo group or an alkyl group on the ring, which are exemplified by the following formulas:

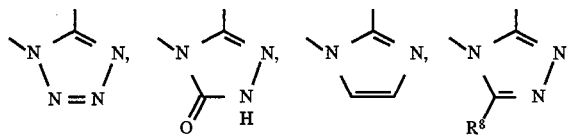

wherein $R^8$ represents a hydrogen atom or an alkyl group.

In the present invention, preferred are compounds represented by general formula (1) or (2), wherein $R^3$ and $R^4$ are combined together to form a bond, $R^2$ represents phenyl group, a substituted phenyl group, a thienyl group, a furyl group, a cycloalkyl group or a cycloalkenyl group, or salts thereof, and compounds represented by general formula (1), wherein $R^6$ and $R^7$ are combined together to form a bond, $R^5$ represents amino group, hydroxyamino group, hydrazino group, an alkylhydrazino group, an acylhydrazino group or an acylamino group, or salts thereof.

Especially preferred is 2-amino-6-chloro-4-phenylquinazoline or salt thereof.

Examples of the salts of the quinazoline compounds which are covered by the present invention include salts with mineral acids such as hydrochloric acid, hydrobromic acid, sulfuric acid or phosphoric acid; salts with organic carboxylic acids such as formic acid, acetic acid, fumaric acid, maleic acid, malic acid, tartaric acid, aspartic acid or glutamic acid; salts with sulfonic acids such as methanesulfonic acid, benzenesulfonic acid, p-toluenesulfonic acid, hydroxybenzenesulfonic acid or dihydroxybenzenesulfonic acid; salts with alkali metals such as sodium or potassium; salts with alkaline earth metals such as calcium or magnesium; salts with organic bases such as trimethylamine, triethylamine or pyridine, or ammonium salts.

The compounds of the present invention include optical isomers and tautomeric isomers. The compounds of the present invention also include all of the hydrates and crystalline forms.

The compounds of the present invention are known compounds and can be synthesized, e.g., by the following processes.

(A) 3,4-Dihydro-2(1H)-quinazolinone compounds can be synthesized, e.g., by the following process.

The compound represented by general formula (5) described below can be synthesized, e.g., by condensing a compound represented by general formula (3) below and an aldehyde represented by general formula (4) below in an inert solvent in the presence of an acid (Japanese Patent Application KOKAI No. 52-51379, Japanese Patent Application KOKOKU Nos. 49-47759, 48-34598, 47-7268 and 47-32995). The compound represented by general formula (3) may be synthesized, e.g., by the following process described in the above publications.

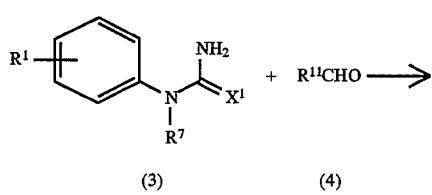

(3)    (4)

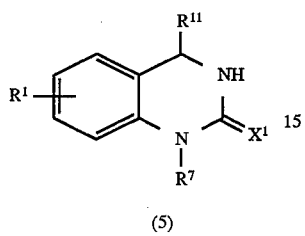

(5)

wherein

R$^1$ and R$^7$ have the same significance as defined above; R$^{11}$ represents a phenyl group, a substituted phenyl group, a thienyl group, a furyl group, a cycloalkyl group, a cycloalkenyl group or an alkyl group; and X$^1$ represents an oxygen atom or a sulfur atom.

The compound represented by general formula (17) below can be synthesized, e.g., by reducing the compound represented by general formula (16) below (Japanese Patent Application KOKAI No. 47-14183, Chem. Pharm. Bull., 29 (8), 2135-2156 (1981)).

The compound represented by general formula (16) may be synthesized, e.g., by the processes described in the publications supra.

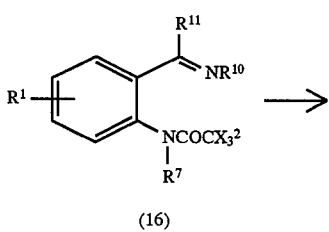

(16)

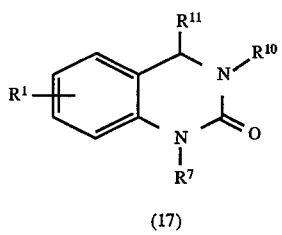

(17)

wherein

R$^1$, R$^7$ and R$^{11}$ have the same significance as defined above; R$^{10}$ represents a hydrogen atom or an alkyl group, and X$^2$ represents a halogen atom.

(B) 2(1H)-Quinazolinone derivatives can be synthesized, e.g., by the following process.

The compound represented by general formula (6) below can be synthesized, e.g., by oxidizing the compound represented by general formula (5) with an oxidizing agent in an inert solvent (Japanese Patent Application KOKAI Nos. 51-8287 and 52-71483, Japanese Patent Application KOKOKU No. 47-48396).

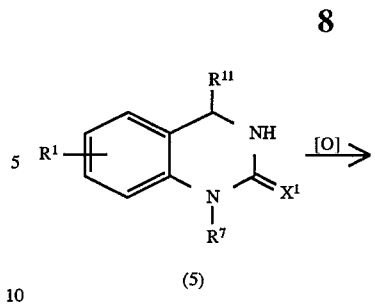

(5)

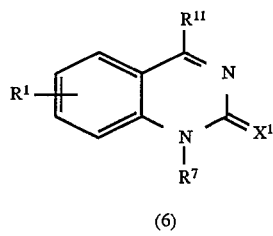

(6)

wherein

R$^1$, R$^7$, R$^{11}$ and X$^1$ have the same significance as defined above.

The compound represented by general formula (8) below can be synthesized, e.g., by reacting the compound represented by general formula (7) with chlorosulfonyl isocyanate, urea or thiourea in an inert solvent (Synthetic Communications, 10 (10), 799–804 (1980), U.S. Pat. No. 3,305,553). The compound represented by general formula (7) below can be synthesized, e.g., by the processes described in the above publications.

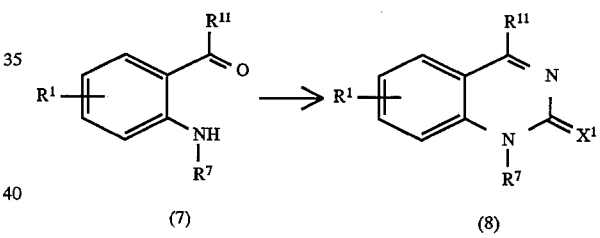

(7)    (8)

wherein

R$^1$, R$^7$, R$^{11}$ and X$^1$ have the same significance as defined above.

The compound represented by general formula (19) below can be synthesized, e.g., by reacting the compound represented by general formula (18) with an organic metallic reagent such as phenyl lithium, phenyl magnesium halide, methyl lithium, a methyl magnesium halide, etc., or with a nucleophilic agent like an amine reagent such as ammonia, hydroxyamine, hydrazine, etc., in an inert solvent (Japanese Patent Application KOKOKU No. 48-21956). The compound represented by general formula (18) can be prepared, e.g., by the process described in the publication supra.

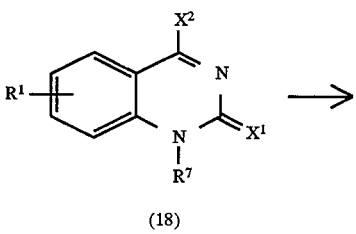

(18)

-continued

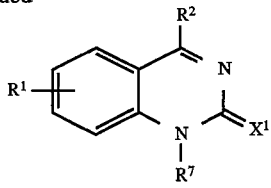

(19)

wherein $R^1$, $R^2$, $R^7$, $X^1$ and $X^2$ have the same significance as defined above.

(C) 2-Substituted quinazoline derivatives can be synthesized, e.g., by the following process.

The compound represented by general formula (10) below can be synthesized, e.g., by reacting the compound represented by general formula (9) with a nucleophilic agent such as ammonia, hydroxyamine, hydrazine, etc., in an inert solvent (U.S. Pat. No. 3,305,553, Japanese Patent Application KOKAI No. 51-100098, Japanese Patent Application KOKOKU No. 45-22135). The compound represented by general formula (9) can be prepared, e.g., by the process described in the publications supra.

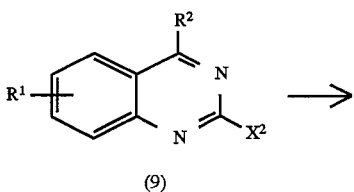

(9)

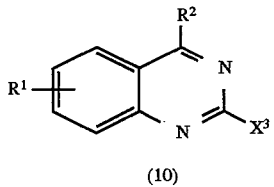

(10)

wherein $R^1$ and $R^2$ have the same significance as defined above; $X^2$ represents a halogen atom; and $X^3$ represents amino group, a hydrazino group, an alkylhydrazino group, an acylhydrazino group, hydroxyamino group or an acylamino group.

The compound represented by general formula (21) below can be synthesized, e.g., by reacting the compound represented by general formula (20) with ammonia in an inert solvent (Ber. Deut. Chem. Ges., 26, 1384–1399 (1893), Chem. Bet., 98, 1049–1059 (1965), Chem. Pharm. Bull., 26 (6), 1633–1651 (1978)). The compound represented by general formula (20) can be prepared, e.g., by the process described in the publications supra.

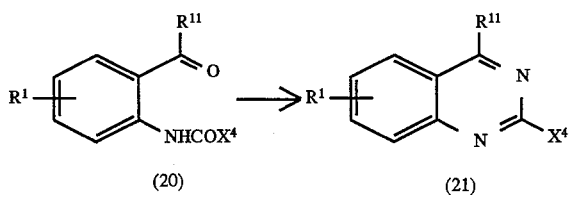

(20)                (21)

wherein $R^1$ and $R^{11}$ have the same significance as defined above, and $X^4$ represents a hydrogen atom, an alkyl group or trifluoromethyl group.

(D) Tetrazoquinazoline derivatives represented by general formula (11) below can be synthesized, e.g., by reacting the compound represented by general formula (9) with sodium azide in an inert solvent (Japanese Patent Application KOKAI No. 53-12893).

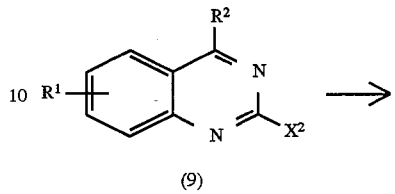

(9)

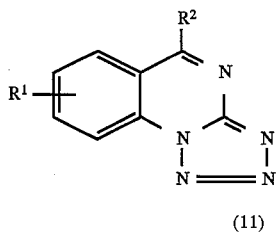

(11)

wherein $R^1$, $R^2$ and $X^2$ have the same significance as defined above.

(E) Imidazoquinazoline derivatives (12) represented by general formula (12) can be synthesized, e.g., by reacting the compound represented by general formula (22) below in an inert solvent in the presence of an acid (Japanese Patent Application KOKAI No. 53-23997). The compound represented by general formula (22) can be synthesized, e.g., by the processes described in the above publications.

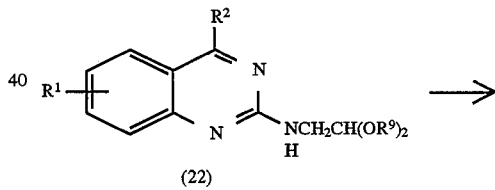

(22)

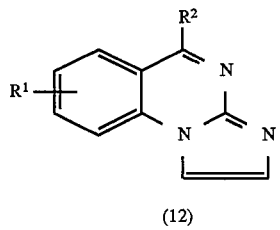

(12)

wherein $R^1$ and $R^2$ have the same significance as defined above; $R^9$ represents an alkyl group.

(F) Triazoquinazoline derivatives represented by general formula (14) can be synthesized, e.g., by reacting, with heating, the compound represented by general formula (13) below in an inert solvent in the presence or absence of an acid (Japanese Patent Application KOKAI No. 51-100098). The compound represented by general formula (13) can be synthesized, e.g., by the processes described in the above publications.

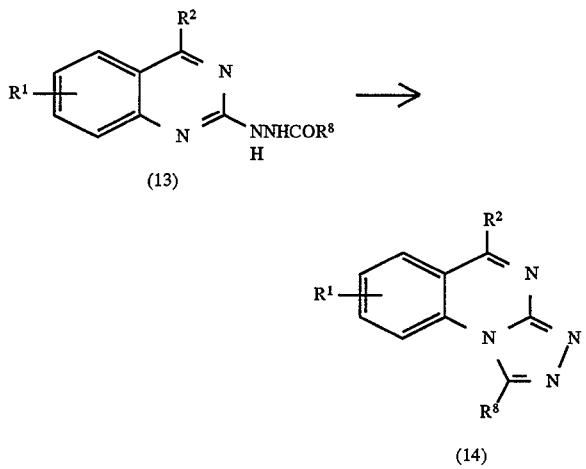

wherein $R^1$, $R^2$ and $R^8$ have the same significance as defined above.

In performing the reactions described hereinabove, where substituent $R^1$ or $R^7$ contains a functional group such as an amino group, a substituted amino group or hydroxy group, these functional groups may be protected prior to perform the reactions above, and the protective groups may then be deprotected to synthesize the objective compounds. Examples of such a protective group for the amino group or substituted amino group include an alkanoyl or aroyl group such as acetyl and benzoyl; examples of a protective group for the hydroxy group include an alkanoyl or aroyl group such as acetyl and benzoyl, or benzyl, methyl, methoxymethyl or trimethylsilyl group (T. W. Greene, "Protective Groups in Organic Synthesis", John Wiley & Sons Inc., 1981).

The active ingredient of the present invention may be administered orally or parenterally. That is, the active ingredient may be administered orally in a conventional form for administration, e.g., in the form of tablets, capsules, syrup or suspension. The active ingredient prepared into a liquid form such as a solution, an emulsion or a suspension may be parenterally administered in the form of injection. The active ingredient may also be administered rectally in the form of a suppository. These pharmaceutical compositions can be prepared in a conventional manner by formulating the active ingredient together with a conventional carrier, excipient, binder, stabilizer, etc. Where the pharmaceutical composition is provided in the form of injection, a buffering agent, a dissolution aid, an isotonic agent or the like may also be added to the composition.

A dose of the composition and the frequency of administration vary depending upon conditions, age, body weight and preparation form. In general, the daily dose of the TNF inhibitor for adult is in the range of 10 to 500 mg for oral administration, or in the range of 1 to 100 mg for parenteral administration, in a single dose or multiple doses.

Hereinafter the present invention will be described in more detail by referring to Preparation Examples and Test Examples but is not deemed to be limited thereto.

PREPARATION EXAMPLE 1

Tablet is prepared, e.g., by the following procedure.

| | Quantity (mg/tablet) |
|---|---|
| Hydrochloride of Compound No. 33 of Test Example 1, later described | 10 |
| Lactose | 72.5 |
| Corn starch | 30 |
| Carboxymethyl cellulose calcium | 5 |
| Hydroxypropyl cellulose (HPC-L) | 2 |
| Magnesium stearate | 0.5 |
| Total | 120 mg |

The respective components are mixed, agglomerated and the resulting mixture is compacted into a tablet of 120 mg.

PREPARATION EXAMPLE 2

Injection is prepared, e.g., by the following procedure.

| | |
|---|---|
| Hydrochloride of Compound No. 36 in Test Example 1, later described | 1 mg |
| Physiological saline | 10 ml |

A solution of the above components is filtered, sterilized and filled in a vial previously washed and sterilized. The vial is plugged with a rubber stopper washed and sterilized, and then sealed with a flip-off-cap to prepare an injection.

TEST EXAMPLE 1

Inhibitory Effect on TNF Formation in Mouse Peritoneal Macrophages

BALB/c mice (5 weeks old, female, Charles River Japan) were intraperitoneally injected with 1 ml of 3% thioglycollate broth. After feeding for 4 days, the mice were sacrificed. Peritoneal exudated cells (PECs) were collected from the peritoneal cavity by washing with minimum essential medium (hereinafter abbreviated as MEM, manufactured by Handai Biseibutubyo Kenkyukai, Osaka, Japan) supplemented with 4 ml of heparin (final concentration of 5 U/ml) and fetal bovine serum (FBS, manufactured by GIBCO Laboratories Inc., final concentration of 1%). PECs were washed three times with MEM, suspended with MEM supplemented with FBS (final concentration of 10%). After the viable cells were counted by exclusion of trypan blue dye, the suspension was adjusted to the final concentration of $2 \times 10^6$ cells/ml with MEM supplemented with FBS and 100 µl each of the dilution was seeded into a 96-well microplate (Costar Company) at $2 \times 10^5$ cells/well. The PECs were incubated for an hour at 37° C. in a humidified 5% $CO_2$ incubator, and then washed twice with MEM warmed at 37° C. to remove non-adherent cells. Residual adherent cells were used as peritoneal macrophages. After the washing above, 50 µl each/well of MEM containing 10% FBS was added to each well and provided for use in the following experiment. Next, the powdery compound of the present invention was dissolved in dimethylsulfoxide in a concentration of 30 mM. The solution was then diluted with MEM supplemented with FBS (final concentration of 10%) in the final concentration of 30 µM or 3 µM. In the peritoneal macrophages obtained above, 50 µl each of the dilution was added to each well to make the total volume 100 µl. Thereafter 100 µl each of lipopolysaccharide (hereinafter abbreviated as LPS, E. coli 0111B4, manufactured by DIFCO, USA) was added to each well in the final concentration of 10 µg/ml. After the cells were incubated at 37° C. for 18 hours in a humidified 5% $CO_2$ incubator, 25 µl of the supernatant in each well was collected.

The TNF activity in the supernatant collected was determined by bioassay using TNF-sensitive mouse fibroblast cell line L929 cells. That is, 100 µl each of MEM containing 10% FBS was added to each well of a 96-well microplate; using the resulting mixture, 25 µl of the collected supernatant was diluted to 5-fold serial dilution to final concentrations (concentrations after the following addition of L929 cell suspension) of 10%, 2%, 0.4% and 0.08%. Then, L929 cells were then suspended in MEM containing FBS (final concentration of 10%) and actinomycin D (Sigma Co., final concentration of 1 µg/ml) and 100 µl each of the suspension was added to each well of the above microplate at $4 \times 10^4$ cells/well and cultured at 37° C. for 18 hours in a humidified 5% $CO_2$. The viable cells were counted by partial modification of the MTT method reported by Monosann et al. (Monosann, T., J. Immunol. Method, 65, 55–63, 1983). That is, 1 mg/ml of 3-(4,5-dimethylthiazol-2-yl)-2,5-diphenyltetrazolium bromide (hereinafter abbreviated as MTT, manufactured by Sigma Co.) was dissolved in MEM, and 50 µl each of the solution was added to each well of the microplate above. After incubating the microplate for further 6 hours, the supernatant was discarded and 100 µl of 0.004N HCl-isopropyl alcohol and then 10 µl of 0.01% sodium laurylsulfate aqueous solution were added to each well. After shaking the 96-well microplate for a few minutes, the absorbance in each well was measured (absorption wavelength of 550 nm) with a microplate reader (Corona Co.). The absorbance correlates to the count of the viable L929 cells and represented the TNF activity in the supernatant. The TNF activity was determined in terms of unit (U)/ml from the calibration curve of absorbance for the TNF activity obtained using mouse recombinant TNF α (TNF-M, manufactured by Genzyme Co.) as a standard. The activity of inhibiting TNF formation of each compound, was determined by the following equation.

Inhibition of TNF formation or secretion (%) =

(1 − TNF activity in the supernatant of the treated cells/TNF activity in the supernatant of the non-treated cells) × 100

The results are shown in Table 1.

TABLE 1

Inhibition of TNF Formation in Mouse Peritoneal Macrophage

| Example No. | Structural Formula | Inhibition of TNF Formation (%) |
|---|---|---|
| 1 | 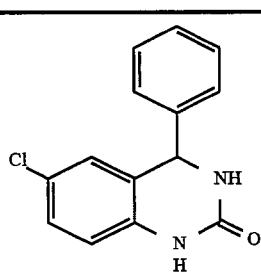 | 79 |
| 2 | 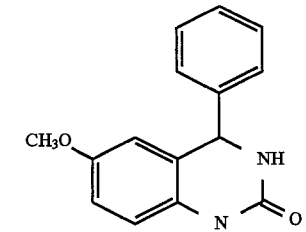 | 42 |
| 3 | 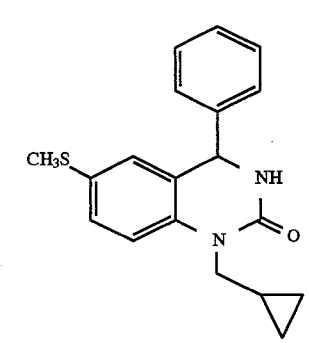 | 53 |
| 4 | 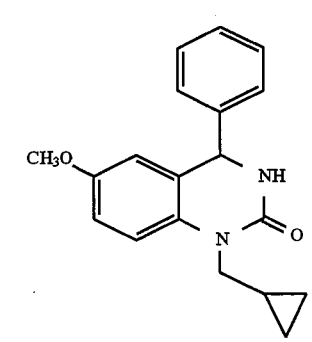 | 76 |
| 5 | 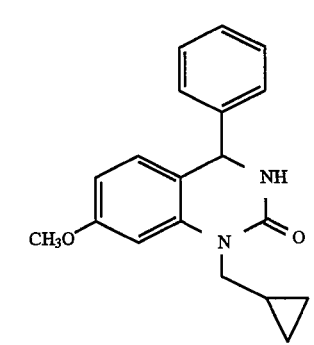 | *54 |

TABLE 1-continued

Inhibition of TNF Formation in Mouse Peritoneal Macrophage

| Example No. | Structural Formula | Inhibition of TNF Formation (%) |
| --- | --- | --- |
| 6 | (structure) | 76 |
| 7 | (structure) | 85 |
| 8 | (structure) | 78 |
| 9 | (structure) | 92 |
| 10 | (structure) | 90 |
| 11 | (structure) | 67 |
| 12 | (structure) | 68 |
| 13 | (structure) | 97 |
| 14 | (structure) | 64 |
| 15 | (structure) | 86 |

TABLE 1-continued

Inhibition of TNF Formation in Mouse Peritoneal Macrophage

| Example No. | Structural Formula | Inhibition of TNF Formation (%) |
|---|---|---|
| 16 | (4-chlorophenyl, phenyl, N-(2-cyclohexylethyl) quinazolinone structure) | −119 |
| 17 | (5-methoxyphenyl, phenyl, N-cyclopropylmethyl quinazolinone structure) | 81 |
| 18 | (phenyl, phenyl, N-cyclopropylmethyl quinazolinone structure) | 59 |
| 19 | (5-methoxyphenyl, 2-thienyl, N-methyl quinazolinone structure) | 87 |
| 20 | (5-chlorophenyl, 2-thienyl, N-methyl quinazolinone structure) | 84 |
| 21 | (5-methoxyphenyl, 2-thienyl, N-CH₂CF₃ quinazolinone structure) | 60 |
| 22 | (5-chlorophenyl, 2-thienyl, N-CH₂CF₃ quinazolinone structure) | 34 |
| 23 | (5-methoxyphenyl, 2-thienyl, N-cyclopropylmethyl quinazolinone structure) | 57 |

TABLE 1-continued

Inhibition of TNF Formation in Mouse Peritoneal Macrophage

| Example No. | Structural Formula | Inhibition of TNF Formation (%) |
|---|---|---|
| 24 | (5-CH₃S-phenyl, 2-thienyl ketimine, N-CH₂-cyclopropyl cyclic urea) | 34 |
| 25 | (5-O₂N-phenyl, 2-thienyl ketimine, N-CH₂-cyclopropyl cyclic urea) | 55 |
| 26 | (5-CH₃O-phenyl, phenyl ketimine, N-CH₂CF₃ cyclic thiourea) | 86 |
| 27 | (5-Cl-phenyl, methyl ketimine, NH cyclic urea) | 39 |
| 28 | (phenyl, methyl ketimine, NH cyclic urea) | 27 |
| 29 | (phenyl, amidine NH₂, NH cyclic urea) | 41 |
| 30 | (5-Cl-phenyl, cyclohexyl ketimine, N-CH₂-cyclopropyl cyclic urea) | 83 |
| 31 | (5-Cl-phenyl, cyclohexyl ketimine, N-CH₂CF₃ cyclic urea) | −7 |
| 32 | (5-CH₃O-phenyl, cyclohexenyl-CH-NH, N-CH₂-cyclopropyl cyclic urea) | 52 |
| 33 | (5-Cl-phenyl, phenyl ketimine, 2-NH₂ dihydroquinazoline) | 98 |
| 34 | (5-Cl-phenyl, phenyl ketimine, 2-NHAc dihydroquinazoline) | 96 |

TABLE 1-continued

Inhibition of TNF Formation in Mouse Peritoneal Macrophage

| Example No. | Structural Formula | Inhibition of TNF Formation (%) |
|---|---|---|
| 35 | (structure: 5-Cl-phenyl with benzoyl, N=C-NHOH) | 98 |
| 36 | (structure: 5-Cl-phenyl with benzoyl, N=C-NHNH$_2$) | 81 |
| 37 | (structure: 5-Cl-phenyl with benzoyl, N=C-NHNHCH$_3$) | 87 |
| 38 | (structure: 5-Cl-phenyl with benzoyl, N=C-Cl) | *49 |
| 39 | (structure: 5-Cl-phenyl with benzoyl, N=CH) | 34 |
| 40 | (structure: 5-CH$_3$O-phenyl with benzoyl, N=C-CF$_3$) | 68 |
| 41 | (structure: phenyl with benzoyl, tetrazole fused) | 83 |
| 42 | (structure: 5-Cl-phenyl with benzoyl, imidazole fused) | *74 |
| 43 | (structure: 6-Cl-phenyl with phenyl, triazinone fused) | *34 |

In the inhibition of TNF formation, the numerical values with asterisk indicate the results obtained with the TNF formation inhibitor in the concentration of 3 µM and the numerical values with no asterisk show the results obtained with the TNF formation inhibitor in the concentration of 30 µM.

TEST EXAMPLE 2

Protective Effect on Endotoxin-Induced Death in Galactosamine-Treated Mice

D-Galactosamine hydrochloride (hereinbelow abbreviated as D-galN, manufactured by Nakarai Tesque) and LPS were dissolved in water at final concentrations of 75 mg/ml and 0.1 or 0.2 µg/ml, respectively. Furthermore, the hydrochloride of Compound No. 33 in Test Example 1 was dissolved in a 5% dimethylsulfoxide-10% Nikkol (Nippon Surfactant Kogyo) solution at the final concentrations of 0, 0.25, 0.5 and 1 mg/ml, respectively.

Next, BALB/c mice (female, 5 weeks old, Charles River Japan, Inc.) were injected i.v. with the aqueous solution containing D-galN and LPS described above in a dose of 200

µl/20 g of body weight. Immediately after the i.v. injection, the animals received i.v. injection with the hydrochloride of Compound No. 33 in Test Example 1 dissolved in the 5% dimethylsulfoxide-10% Nikkol solution in the concentration above in a dose of 200 µl/20 g of body weight.

The activity of the compound for protection of endotoxin-induced death in the galactosamine-treated mice is expressed in terms of the survival rate observed for the following last 7 days (a mean value of 3 runs).

Figure 1:
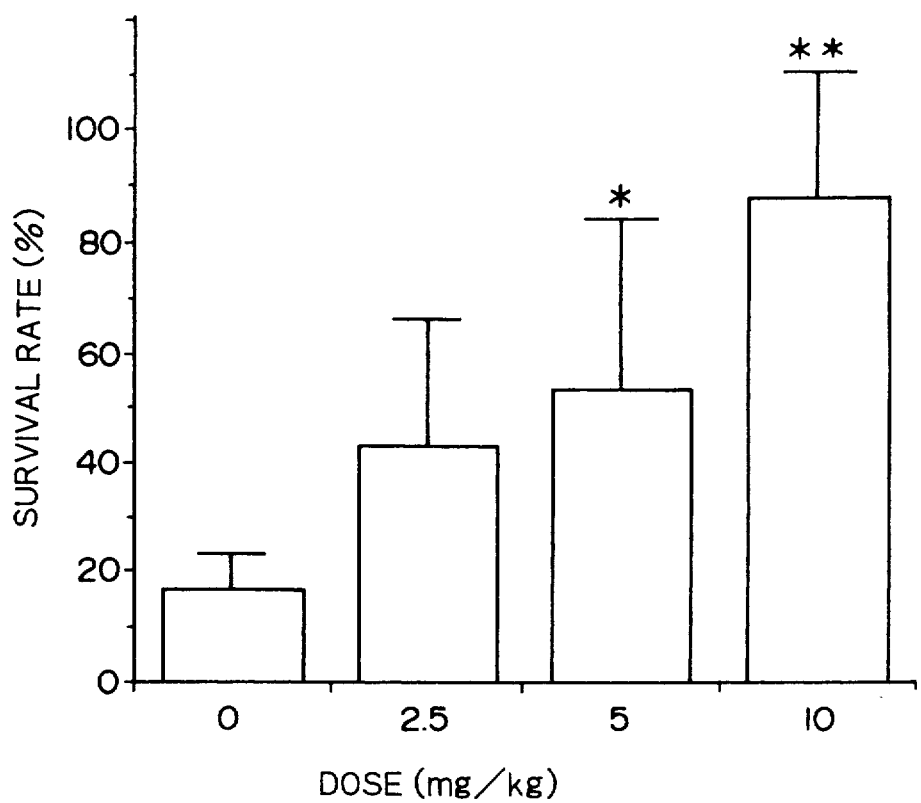
FIG. 1 is a graph showing the results of a test performed in Test Example 2 herein, in which a protective effect on endotoxin-induced death in galactosamine-treated mice was examined.

As shown in FIG. 1, the hydrochloride of Compound No. 33 in Test Example 1 significantly retarded the death caused by endotoxic shock in galactosamine-treated mice in a dose of 5 mg/kg or more (Student t test was performed between the group administered with no compound and the group administered with the compound).

TEST EXAMPLE 3

Inhibition of TNF Formation in Endotoxin Shock in Galactosamine-Treated Mice D-galN and LPS were dissolved in water at final concentrations of 75 mg/ml and 0.2 µg/ml, respectively. Furthermore, the hydrochloride of Compound No. 33 in Test Example 1 was dissolved in a 5% dimethylsulfoxide-10% Nikkol solution at the final concentrations of 0.5, 1 and 2.5 mg/ml, respectively.

Next, BALB/c 63 mice were divided into four groups of 18, 15, 15 and 15 mice (named Groups A, B, C and D in order). All groups received i.v. injection of the aforesaid aqueous solution containing D-galN and LPS in a dose of 200 µl/20 g of body weight. Immediately after the i.v. injection, Group A received i.v. injection of the 5% dimethylsulfoxide-10% Nikkol solution as a control; and Groups B, C and D received i.v. injection of the hydrochloride of Compound No. 33 in Test Example 1 in the concentrations of 0.5, 1 and 2.5 mg/ml, respectively, in a dose of 200 µl/20 g of body weight.

In Group A, serum was separated from blood collected from the heart of 3 mice immediately after administration of the 5% dimethylsulfoxide-10% Nikkol solution and collected at the time periods of 0.5, 1, 1.5, 3 and 5 hours after the administration. Blood was also collected in Groups B, C and D as in Group A, at the time periods of 0.5, 1, 1.5, 3 and 5 hours after the administration of the compound to obtain serum. All serum were sterilized by filtration and then stored at −20° C. until the following procedures were performed.

The TNF activity in the serum collected was determined by bioassay using L929 cells in a manner similar to Test Example 1. That is, the serum was diluted to 3-fold serial dilution in a test tube using MEM containing FBS (final concentration of 10%) to make the final concentrations (concentrations after the following addition of L929 cell suspension) of 5, 1.7, 0.6 and 0.2%. Then 100 µl each of the diluted serum was added to each well of a 96-well microplate. Then, L929 cells were suspended in MEM containing FBS (final concentration of 10%) and actinomycin D (Sigma Co., final concentration of 1 µg/ml) and 100 µl each of the suspension was added to each well of the above microplate at $4\times10^4$ cells/well, followed by culturing at 37° C. for 18 hours in a humidified 5% $CO_2$. The viable cells were counted by partial modification of the MTT method described above. The TNF activity was determined using mouse recombinant TNF α as a standard.

As shown in FIG. 2, a temporary increase of the TNF activity in blood after the administration of D-galN/LPS was noted in the control group. The hydrochloride of Compound No. 33 in Test Example 1 significantly suppressed the aforesaid increase in blood TNF level dose-dependently at a dose of 1 mg/kg or more (Student t test was performed in the TNF activity between the control group and the compound group at the same passage time).

INDUSTRIAL APPLICABILITY

The compounds represented by general formula (1) or general formula (2) have the activity of significantly inhibiting the production or secretion of TNF. Accordingly, these compounds are effective for the treatment of diseases including cachexia, sepsis or multiple organ failure wherein a tumor necrosis factor is considered to be involved in causing those diseases.

We claim:

1. A method of inhibiting tumor necrosis factor formation and/or secretion comprising the step of administering an effective amount of a pharmaceutical composition comprising as an active ingredient a compound represented by formula (1)

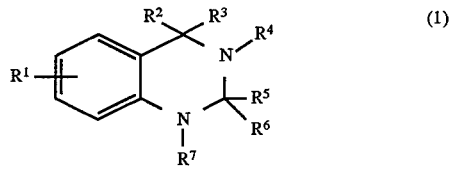

wherein $R^1$ represents a hydrogen atom, a halogen atom, a hydroxy group, an amino group, a substituted amino group, a nitro group, a cyano group, an alkyl group, an alkoxy group, an alkylthio group, an acyl group, a carboxyl group or an alkoxycarbonyl group; $R^2$ represents a phenyl group, a substituted phenyl group, a thienyl group, a furyl group, a cycloalkyl group, a cycloalkenyl group, an alkyl group, an amino group or a substituted amino group; $R^3$ represents a hydrogen atom and $R^4$ represents a hydrogen atom or an alkyl group, or $R^3$ and $R^4$ are combined together to form a bond; in $R^5$, $R^6$ and $R^7$, $R^5$ and $R^6$ are combined together to form an oxo group or a thioxo group and $R^7$ represents a hydrogen atom, an alkyl group, a haloalkyl group, a phenyl group, a substituted phenyl group or a group shown by formula: —X—Y (wherein X represents an alkylene group and Y represents a cycloalkyl group, a phenyl group, a substituted phenyl group, a carboxyl group, a hydroxy group, an alkoxy group, an aminocarbonyl group, a substituted aminocarbonyl group, an alkoxycarbonyl group, an amino group or a substituted amino group), or, $R^6$ and $R^7$ are combined together to form a bond and $R^5$ represents a hydrogen atom, an alkyl group, an amino group, a halogen atom, a haloalkyl group, a hydroxyamino group, a hydrazino group, an alkylhydrazino group, an acylhydrazino group or an acylamino group; or a compound represented by formula (2)

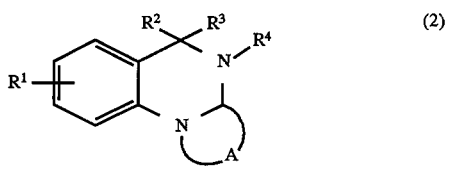

wherein $R^1$, $R^2$, $R^3$ and $R^4$ have the same definitions as described above and the formula therein:

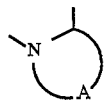

represents a heterocyclic group containing 2 to 4 nitrogen atoms; or a salt thereof.

2. A method of inhibiting tumor necrosis factor formation and/or secretion according to claim 1, which comprises as said active ingredient a compound represented by formula (1) or (2), wherein $R^3$ and $R^4$ are combined together to form a bond, and $R^2$ is a phenyl group, a substituted phenyl group, a thienyl group, a furyl group, a cycloalkyl group or a cycloalkenyl group, or a salt thereof.

3. A method of inhibiting tumor necrosis factor formation and/or secretion according to claim 1, which comprises as said active ingredient a compound represented by formula (1), wherein $R^6$ and $R^7$ are combined together to form a bond, and $R^5$ is an amino group, a hydroxyamino group, a hydrazino group, an alkylhydrazino group, an acylhydrazino group or an acylamino group, or a salt thereof.

4. A method of inhibiting tumor necrosis factor formation and/or secretion according to claim 1, which comprises 2-amino-6-chloro-4-phenylquinazoline or a salt thereof as said active ingredient.

* * * * *

UNITED STATES PATENT AND TRADEMARK OFFICE
CERTIFICATE OF CORRECTION

PATENT : 5,646,154

DATED : July 8, 1997

INVENTOR(S) : Kenji Irie et al

It is certified that error appears in the above-identified patent and that said Letters Patent is hereby corrected as shown below:

In the Drawings:

Delete drawing Sheet 1, consisting of FIGS. 15, 16, 17 and 18, and substitute therefor the drawing Sheet consisting of FIG. 1, as shown on the attached page.

Signed and Sealed this

Thirtieth Day of December, 1997

*Attest:*

BRUCE LEHMAN

*Attesting Officer*     Commissioner of Patents and Trademarks

PROTECTIVE EFFECT ON ENDOTOXIN—INDUCED DEATH IN GALACTOSAMINE—TREATED MICE

\* : p<0.05,  \*\* : p<0.01